United States Patent [19]
Onodera et al.

[11] Patent Number: 4,822,783
[45] Date of Patent: Apr. 18, 1989

[54] METHOD FOR TREATING HTLV-I USING STREPTOVARICIN C COMPOUNDS

[75] Inventors: Kazukiyo Onodera, Tokyo; Shinichi Ito, Tokorozawa, both of Japan

[73] Assignee: Shin-Etsu Chemical Co., Ltd., Tokyo, Japan

[21] Appl. No.: 137,824

[22] Filed: Dec. 24, 1987

[30] Foreign Application Priority Data

Dec. 27, 1986 [JP] Japan .................. 61-313463

[51] Int. Cl.$^4$ .................. A61K 31/395; C07D 491/08
[52] U.S. Cl. ..................... 514/183; 540/456
[58] Field of Search .................. 540/456; 514/183

[56] References Cited

U.S. PATENT DOCUMENTS 4,212,881 7/1980 Sasaki et al. .................. 540/456

OTHER PUBLICATIONS

Miyoshi et al, *Nature*, vol. 294, No. 5843, Dec. 1981, pp. 770–771.

Primary Examiner—Mary C. Lee
Assistant Examiner—Zinna Nothington
Attorney, Agent, or Firm—Oblon, Fisher, Spivak, McClelland & Maier

[57] ABSTRACT

An anti-HTLV-I agent comprising as an effective component a streptovaricin C derivative represented by the general formula (I):

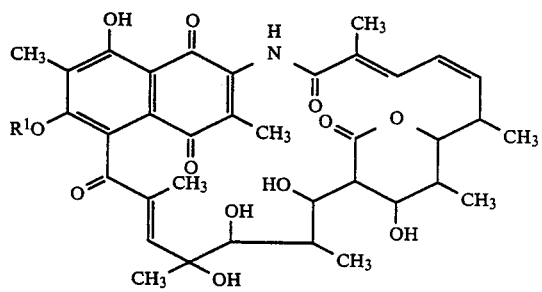

wherein $R^1$ represents an alkyl group having 3 to 7 carbon atoms.

The streptovaricin C derivative has good HTLV-I killing activity, and this agent is useful for therapy of diseases caused by HTLV-I.

5 Claims, 1 Drawing Sheet

METHOD FOR TREATING HTLV-I USING STREPTOVARICIN C COMPOUNDS

BACKGROUND OF THE INVENTION

1. Field of the Invention

This invention relates to an anti-HTLV-I agent.

2. Description of the Prior Art

Any effective therapeutic method for diseases caused by HTLV-I (Human T lymphotropic virus type I), such as adult T cell leukemia/lymphoma (ATL) has not yet been established.

U.S. Pat. No. 4,212,881 discloses that streptovaricin C derivatives represented by the general formula

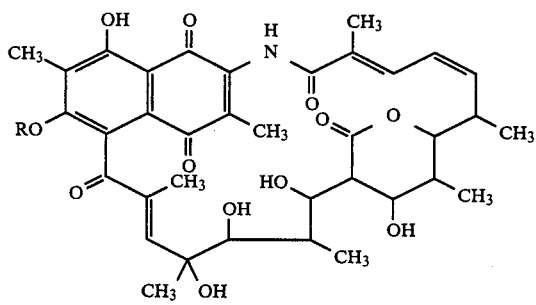

wherein R represents an allyl, cyclopentyl, cyclohexyl or adamanthyl group or a $C_1$, -$C_{20}$ alkyl group which can be substituted with hydroxyl, cyano, acetyl, formyl, furoyl, thenoyl, methoxy, carbamyl, phenyl or phenyl group substituted with nitro or ethyl or a phenacyl group which can be substituted with a halogen, methoxy or phenyl group,
have anti-tumour virus activities in mice. However, it has not hitherto been known that any of these streptovaricin C derivatives have activities killing cells infected with HTLV-I.

SUMMARY OF THE INVENTION

The present inventors have discovered that a certain kind of the streptovaricin C derivatives described above has excellent killing activity against cells infected with HTLV-I.

Based on the above discovery, an object of the present invention lies in providing a novel anti-HTLV-I agent useful for therapy of diseases caused by HTLV-I.

Another object of the present invention is to provide a method for treating the diseases caused by HTLV-I, and a further object is to provide a use of a compound or a composition containing the compound for the manufacture of a medicament for therapy of the diseases caused by HTLV-I.

Thus the present invention provides an anti-HTLV-I agent comprising, in an effective amount, a streptovaricin C derivative represented by the general formula (I):

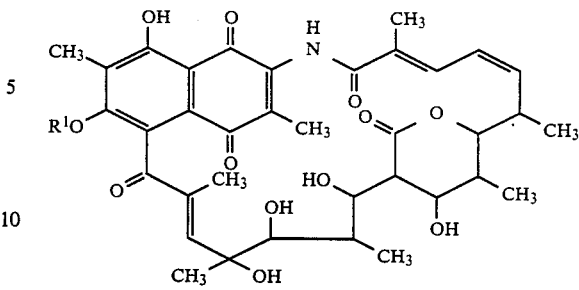

wherein $R^1$ represents an alkyl group having 3 to 7 carbon atoms.

The present invention also provides a method for treating the diseases caused by HTLV-I with use of said streptovaricin C derivative. And the invention provides a use of said streptovaricin C derivative for manufacture of a medicament for therapy of the diseases caused by HTLV-I.

The streptovaricin C derivative used in the present invention has activities remarkably killing cells infected with HTLV-I and therefore the agent of the invention is useful for therapy of the diseases caused by HTLV-I, such as ATL.

DETAILED DESCRIPTION OF THE INVENTION

Figure 1:
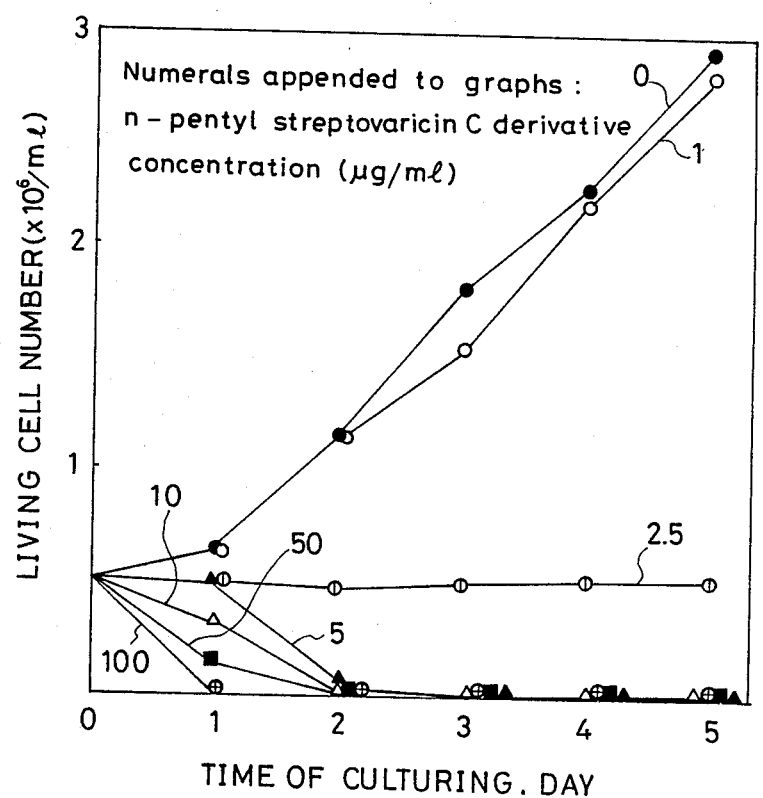
FIG. 1 illustrates the results of culturing of HTLV-I infected cells in the presence of N-pentylstreptovaricin C derivative in various concentrations, as obtained in Example.

Examples of the alkyl group having 3 to 7 carbon atoms in the definition of $R^1$ in the general formula (I) include a propyl, butyl, pentyl, hexyl and heptyl group. Preferred is n-pentyl group.

The streptovaricin C derivative of the general formula (I) has low toxicities against HTLV-I-noninfected mammalian cells, and also in this point, the anti-HTLV-I agent of the present invention is excellent.

The streptovaricin C derivative of the general formula (I) has extremely low acute toxicities, and for example, in the case of the derivative having methyl group as the $R^1$ at C-19 position in the general formula (I), 50% lethal dose ($LD_{50}$) against mouse is 1,000 mg/kg or more in intramuscular administration and 3,000 mg/kg or more in oral administration.

The streptovaricin C derivative of the general formula (I) as used in the present invention itself is known, for example, in U.S. Pat. No. 4,212,881, and preparation, isolation and purification thereof can be carried out according to the methods described in the patent.

According to the preparation method disclosed in the above U.S. Pat. No. 4,212,881, the streptovaricin C derivative of the general formula (I) can be prepared by hydrolysis of streptovaricin C in a mild oxidizing condition to produce a streptovaricin C derivative corresponding the compound of the general formula (I) wherein $R^1$ is hydroxyl group together with damavaricin C, and subjecting the streptovaricin C derivative thus obtained to etherification of the phenolic hydroxyl group at the C-19 position.

The streptovaricin C derivative of the general formula (I) is generally obtained in the form of a mixture of two kinds of optical isomers known as damavaricin Fc derivative and atropisodamavaricin Fc derivative. The damavaricin Fc derivative has P-helicitic structure in which a double bond of C(15)=C(16) is disposed at upper side of carbonyl group C(24)=O in stereomatic structure to the single bond C(17)-C(18) in the same manner as in streptovaricin C, whereas atropisodamavaricin Fc has M-helicitic structure in which the double bond is stereomatically in opposite position.

The anti-HTLV-I agent of the present invention may variously be prepared as a pharmaceutical composition by compounding said streptovaricin C derivative with, for example, organic or inorganic solid or liquid vehicles. Examples of preferred vehicles include water, gelatin, lactose, starch, calcium carboxymethylcellulose, microcrystalline cellulose, stearyl alcohol, magnesium stearate, talc, vegetable oils, benzyl alcohol, propylene glycol, gum, polyalkylene glycol, white petrolatum, jelly, cholesterol and the like. Pharmaceuticals thus prepared may be in any form such as powder, tablet, granule, sugar-coated tablet, suppository, pill, capsule, liquid, suspension, ampoule, emulsion and injection. These pharmaceutical compositions may contain various adjuvants, for example, preservatives, stabilizers, wetting agents, emulsifying agents, solubilizing agents, salts for osmotic pressure adjustment, buffers, binding agents, suspending and dispersing agents, lubricants and the like, and can conventionally be prepared.

The desirable dose of the anti-HTLV-I agent of the present invention depends on, for example, race, age, body weight and the like as well as administration method. The dose thereof per day for an adult is generally 1 to 100 mg/kg, preferably 5 to 50 mg/kg in the case of parenteral administration, and is generaly 1 to 1,000 mg/kg, preferably 25 to 500 mg/kg in the case of oral administration, respectively as the streptovaricin C derivative of the general formula (I).

The typical examples of the diseases caused by HTLV-I include ATL, HTLV-I associated myelopathy (HAM) and tropical spastic paraparesis.

The present invention is explained in detail below by an example.

EXAMPLE (1) HTLV-I infected human lymphocytes known as MT-4 (see Miyoshi, I. et al., Nature 294 p. 770 (1981)) were suspended at a concentration of $5 \times 10^5$ cells/ml in each of five kinds of 10% fetal bovine serum-supplemented 1640 media each containing 0, 1, 2.5, 5, 10, 50 or 100 μg/ml of n-pentylstreptovaricin C derivative (the compound of the general formula (I) wherein R is n-pentyl group), and cultured at 37° C. under 5% $CO_2$. Suspended cells were sampled at regular intervals, subjected to trypan blue staining and measured for living cell number and dead cell number with a microscope. Changes of the living cell number in the media thus determined are shown in FIG. 1.

As FIG. 1 shows, in concentrations of n-pentylstreptovaricin C derivative of 1 μg/ml or less, the number of the living MT-4 cells increased with the lapse of time. In 2.5 μg/ml, the living cell number was almost unchanged during the culturing, and in 5 μg/ml or more, the living cell number decreased and the cells almost completely died out 2 days after the start of the culturing.

(2) Culturing and measurment for living cell number and dead cell number were carried out in the same manner as described above except that HTLV-I-noninfected human leukemia cells ($P_3HR_1$, MLT-6, ALL-6 and MOLT-4B) were cultured in place of MT-4 cells in the same media containing 5 μg/ml of n-pentylstreptovaricin C derivative as used above. The proportion of living cells among the entire cells was 90 to 98% at the time of the start of culturing. The proportion was almost unchanged two days after the start of culturing and 75 to 90% four days after the start of culturing. These results show that n-pentylstreptovaricin C derivative has low inhibiting activity against the growth of HTLV-I-noninfected human leukemia cells.

(3) Culturing and measurement of living cells and dead cells were carried out in the same manner as described in above (1), except that normal human lymphocytes were cultured in place of MT-4 cells. The growth of the normal lymphocytes was not inhibited by n-pentylstreptovaricin C derivative.

It can be understood from the results above that n-pentylstreptovaricin C derivative exhibits marked killing-activity against HTLV-I-infected leukemia cells at a concentration of 5 μg/ml or more but is not toxic against virus-unrelated leukemia cells or normal cells.

What we claim is:

1. A method for treating a disease caused by HTLV-I which comprises treating a patient suffering from a disease caused by HTLV-I with an effective dose of a damavaricin Fc derivative represented by the formula (I):

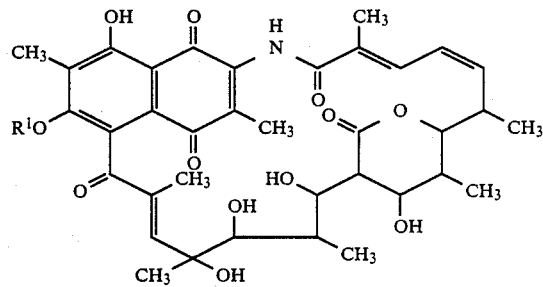

wherein $R^1$ represents an alkyl group having 3 to 7 carbon atoms.

2. The method of claim 1, wherein $R^1$ in the formula (I) is n-pentyl group.

3. The method of claim 1, wherein said disease is adult T cell leukemia/lymphoma.

4. The method of claim 1, wherein said disease is HTLV-I associated myelopathy.

5. The method of claim 1, wherein said disease is tropical spastic paraparesis.

* * * * *